United States Patent
Cooks et al.

(10) Patent No.: US 10,168,312 B2
(45) Date of Patent: Jan. 1, 2019

(54) SYSTEMS AND METHODS FOR SCREENING A SAMPLE BASED ON MULTIPLE REACTION MONITORING MASS SPECTROMETRY

(71) Applicant: Purdue Research Foundation, West Lafayette, IN (US)

(72) Inventors: Robert Graham Cooks, West Lafayette, IN (US); Christina Ramires Ferreira, West Lafayette, IN (US); Tiago Sobreira, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 15/649,763

(22) Filed: Jul. 14, 2017

(65) Prior Publication Data
US 2018/0024108 A1    Jan. 25, 2018

Related U.S. Application Data

(60) Provisional application No. 62/365,618, filed on Jul. 22, 2016.

(51) Int. Cl.
*H01J 49/42* (2006.01)
*G01N 33/48* (2006.01)
(Continued)

(52) U.S. Cl.
CPC ..... *G01N 33/487* (2013.01); *G06F 17/30592* (2013.01); *H01J 49/005* (2013.01);
(Continued)

(58) Field of Classification Search
CPC ............ G01N 33/487; G01N 2560/00; G01N 2570/00; G01N 2800/2835;
(Continued)

(56) References Cited

U.S. PATENT DOCUMENTS

| 5,644,131 A | 7/1997 | Hansen |
| 6,838,666 B2 | 1/2005 | Ouyang et al. |

(Continued)

FOREIGN PATENT DOCUMENTS

| WO | 2009/102766 A1 | 8/2009 |
| WO | 2018/004769 A2 | 1/2018 |

OTHER PUBLICATIONS

Jimenez-Jimenez et al, "Cerebrospinal Fluid Biochemical Studies in Patients with Parkinson's Disease: Toward a Potential Search for Biomarkers for this Disease", Fron. Cell. Neurosci. Nov. 11, 2014.*
(Continued)

*Primary Examiner* — David E Smith
(74) *Attorney, Agent, or Firm* — Purdue Research Foundation

(57) ABSTRACT

The invention generally relates to systems methods for screening a sample based on multiple reaction monitoring mass spectrometry. In certain embodiments, the invention provides methods for screening a sample that involve ionizing a sample. Mass spectrometry is then used in order to monitor specific transitions connecting one or more ion pairs within the sample in order to generate a multidimensional chemical profile of the sample. Then, the multidimensional chemical profile of the sample is compared to a database of reference multidimensional chemical profiles, thereby screening the sample. Each reference multidimensional chemical profile is produced from a training set of data.

12 Claims, 11 Drawing Sheets

(51) Int. Cl.
  *G01N 33/487* (2006.01)
  *G06F 17/30* (2006.01)
  *H01J 49/00* (2006.01)
  *H01J 49/16* (2006.01)
  *H04L 1/00* (2006.01)
  *G06F 19/00* (2018.01)

(52) U.S. Cl.
  CPC ........ *H01J 49/0036* (2013.01); *H01J 49/165* (2013.01); *H01J 49/424* (2013.01); *H04L 1/0072* (2013.01); *G01N 2560/00* (2013.01); *G01N 2570/00* (2013.01); *G01N 2800/2835* (2013.01); *G06F 19/324* (2013.01)

(58) Field of Classification Search
  CPC  G06F 17/30592; G06F 19/324; H01J 49/005; H01J 49/0036; H01J 49/165; H01J 49/424
  See application file for complete search history.

(56) References Cited

U.S. PATENT DOCUMENTS

| | | | |
|---|---|---|---|
| 7,335,897 B2 | 2/2008 | Takats et al. | |
| 8,859,956 B2 | 10/2014 | Ouyang et al. | |
| 2003/0224386 A1* | 12/2003 | Guild | C07K 14/4713 435/6.11 |
| 2006/0195269 A1 | 8/2006 | Yeatman et al. | |
| 2009/0081713 A1* | 3/2009 | Klein | G01N 33/6893 435/7.92 |
| 2014/0235473 A1* | 8/2014 | Otto | C07K 14/8125 506/9 |
| 2014/0264004 A1 | 9/2014 | Cooks et al. | |

OTHER PUBLICATIONS

Roede et al, "Serum Metabolomics of Slow vs. Rapid Motor Progression Parkinson's Disease: a Pilot Study", PLOS One vol. 8 Issue Oct. 10, 2013.*
Nikas et al., Am J Transl Res. Feb. 15, 2011; 3(2): 180-196.
Yamashita et al., J. Phys. Chem., 88:4451-4459, 1984.
Laiko et al. Anal. Chem., 72:652-657, 2000.
Tanaka et al. Rapid Commun. Mass Spectrom., 2:151-153, 1988.
Kogelschatz, Plasma Chemistry and Plasma Processing, 23:1-46, 2003.
Shiea et al., J. Rapid Communications in Mass Spectrometry, 19:3701-3704, 2005.
Takats et al. Anal. Chem., 2004, 76 (14), pp. 4050-4058.
Sao et al. Anal. Chem. 2008, 80, 7198-7205.
Bonner et al., International Journal of Mass Spectrometry and Ion Physics, 24(3):255-269, 1977.
Hagar, Rapid Communications in Mass Spectrometry, 16(6):512-526, 2002.
M. de Raad et al., Curr Opin Chem Biol, 2016, 30, 7-13.
Cooks, et al., Science, 2006, 311, 1566-70.
Ifa and Eberlin, Clin Chem, 2016, 62, 111-23.
Jarmusch, et L., Proc Natl Acad Sci U S A, 2016, 113, 1486-91.
Massano and Bhatia, Cold Spring Harb Perspect Med, 2012, 2, a008870.
Kang, et al., Acta Neuropathol, 2016, DOI: 1007/s00401-016-1552-2.
Harrington, et al., Cerebrospinal fluid sodium rhythms, Cerebrospinal Fluid Res, 2010, 7, 3.
Hughes, et al., J Neurol Neurosurg Psychiatry, 1992, 55, 181-4.
Wei, et al., Anal Chem, 2010, 82, 5527-5533.
Xia, et al., Nucleic Acids Res, 2015, 43, W251-7.
Kuiper, et al., Neural Transm (Vienna), 2000, 107, 183-9.
Lewandowski, et al., Proc Natl Acad Sci U S A, 2010, 107, 16970-16975.
Roede, et al., PLoS One, 2013, 8, e77629.
Karas, 2000, Nano-electrospray ionization mass spectrometry: addressing analytical problems beyond routine, Fresenius J. Anal. Chem., vol. 366: pp. 669-676.
Schlossmacher, 2010, Biomarker research in Parkinson's[euro][TM]s disease: objective measures needed for patient stratificationin future cause-directed trials, Bioarmers in Medicine, vol. 4, No. 5: pp. 647.
Robitti, 2014, Biomarkers Discovery through Multivariate Statistical Methods: A Review of Recently Developed Methods and Applications in Proteomics, J. Proteomics Bioinform. S3:003.
Pan, 2004, Nanoelectrospray Ionization of Protein Mixtures: Solution pH and Protein pI, Anal. Chem, vol. 76: pp. 1165-1174.

* cited by examiner

SYSTEMS AND METHODS FOR SCREENING A SAMPLE BASED ON MULTIPLE REACTION MONITORING MASS SPECTROMETRY

RELATED APPLICATION

The present application claims the benefit of and priority to U.S. provisional application Ser. No. 62/365,618, filed Jul. 22, 2016, the content of which is incorporated by reference herein in its entirety.

FIELD OF THE INVENTION

The invention generally relates to systems and methods for screening a sample based on multiple reaction monitoring mass spectrometry.

BACKGROUND

The workflow often used for conventional screening of complex samples by mass spectrometry (MS) is selective and time consuming since it includes sample preparation procedures such as extraction and derivatization, followed by chromatographic separation before ionization and data acquisition. In order to obtain molecular structural information, high resolution MS or fragmentation of mass selected ions can be performed. Statistical univariate analysis is then used to evaluate the value of each metabolite as an individual biomarker.

SUMMARY

The invention provides an accelerated workflow for analysis of complex chemical or biochemical samples and results of sample screening by mass spectrometry based on multiple reaction monitoring (MRM). Analytes present in a complex sample (e.g., a chemical, biochemical, or biological sample) are monitored using specific transitions connecting ion pairs. A set of such transitions constitutes a multidimensional chemical profile used to distinguish and characterize different samples using multivariate statistical methods. While exemplified for analysis of Parkinson's disease, the systems and methods herein can be applied for screening of any type of sample, such as a chemical, biochemical, or biological sample. The analyte to be detected can be at any level within the sample. In certain embodiments, the analytes are major sample components. In other embodiments, the analyte of interest is at low parts per million levels.

In certain aspects, the invention provides a method for screening a complex sample, such as a chemical, biochemical, or biological sample, that involves ionizing a sample. Specific transitions connecting one or more ion pairs within the sample are monitored by mass spectrometry in order to generate a multidimensional chemical profile of the sample. The multidimensional chemical profile of the sample is then compared to a database of reference multidimensional chemical profiles, thereby screening the biological sample. Each reference multidimensional chemical profile is produced from a training set of data. The set of transitions which produces the training set data are chosen using a supervised set of precursor and neutral loss scans chosen to cover the likely functional groups in the classes of compounds represented by the sample. This small set of scans can be acquired rapidly, compared to a totally unsupervised acquisition of the entire MS/MS data domain. In the context of biological samples, the training set of data may be from a population of patients with a known disease status. In certain embodiments, the ion pairs are connected by fragmentation.

Other aspects of the invention provide methods for screening a complex sample that involve receiving to a computer mass spectrometry data on a sample obtained by multiple reaction monitoring. The mass spectrometry data includes specific transitions connecting one or more ion pairs within the sample. The method then involves applying via the computer an unsupervised multivariate analysis to the mass spectrometry data in order to generate a multidimensional chemical profile of the sample. The method then involves comparing via the computer the multidimensional chemical profile of the sample to a database of reference multidimensional chemical profiles, in which each reference multidimensional chemical profile is produced from a training set of data. In the context of biological samples, the training set of data may be from a population of patients with a known disease status. In certain embodiments, prior to the receiving step, the method further involves ionizing the sample to produce an ionized sample, and analyzing the ionized sample using multiple reaction monitoring mass spectrometry.

Any ionizing technique known in the art can be used with the methods of the invention and exemplary ionizing techniques are ambient ionization techniques, such as paper spray ionization or electrosonic spray ionization.

In certain embodiments, the sample is a biological sample. Typically, the biological sample is a human tissue or body fluid sample. Generally, a body fluid refers to a liquid material derived from, for example, a human or other mammal. Such body fluids include, but are not limited to, mucus, blood, plasma, serum, serum derivatives, bile, phlegm, saliva, sweat, amniotic fluid, mammary fluid, urine, sputum, and cerebrospinal fluid (CSF), such as lumbar or ventricular CSF. A body fluid may also be a fine needle aspirate. A body fluid also may be media containing cells or biological material.

In certain embodiments, the human tissue or body fluid sample is a cerebrospinal fluid sample. In such embodiments, the cerebrospinal fluid sample may be screened for Parkinson's disease. This methodology shows promising initial results for the currently unsolved challenge of Parkinson's disease (PD) laboratory diagnosis by biomarker screening. In certain embodiments, the multidimensional chemical profile of the sample includes a sum of an abundance of each of the ion pairs selected from the group consisting of: 134.1→72.4; 177→141.1; 76.2→59.4; and 184→125.2, divided by an abundance of the ion pair 188→171. In other embodiments, the multidimensional chemical profile of the sample includes an abundance of only the ion pair 188→171. The ion pair 188→171 represents N8- or N1-acetylspermidine.

BRIEF DESCRIPTION OF THE DRAWINGS

FIG. 2 panel A shows PCA analysis (autoscaled data) as the combination of principal components 1 and 2 and indicates some tendency to discriminate PD (green dots) from HC (red dots). The variables used for the PC were the MRMs consistent with the assignment as N-acetylspermidine and six other combinations of MRMss (Table 3). FIG. 2 panel B shows that the log 2 (fold change) for HC/PD was −0.4 for the MRM transition that corresponds to Nacetylspermidine. FIG. 2 panel C shows that the resulting multivariate ROC curve (built using PLS-DA as the algorithm) constructed with the testing sample set (N=60; 230 measurements) had an area under the curve (AUC) of 0.8. This ROC curve was used to classify the validation samples (N=60; 180 measurements). FIG. 2 panel D shows the univariate ROC distribution and threshold for the MRM of N-acetylspermidine and for the best achieved MRM combination.

(FIG. 5D) years of symptoms at CSF collection.

DETAILED DESCRIPTION

Figure 1:
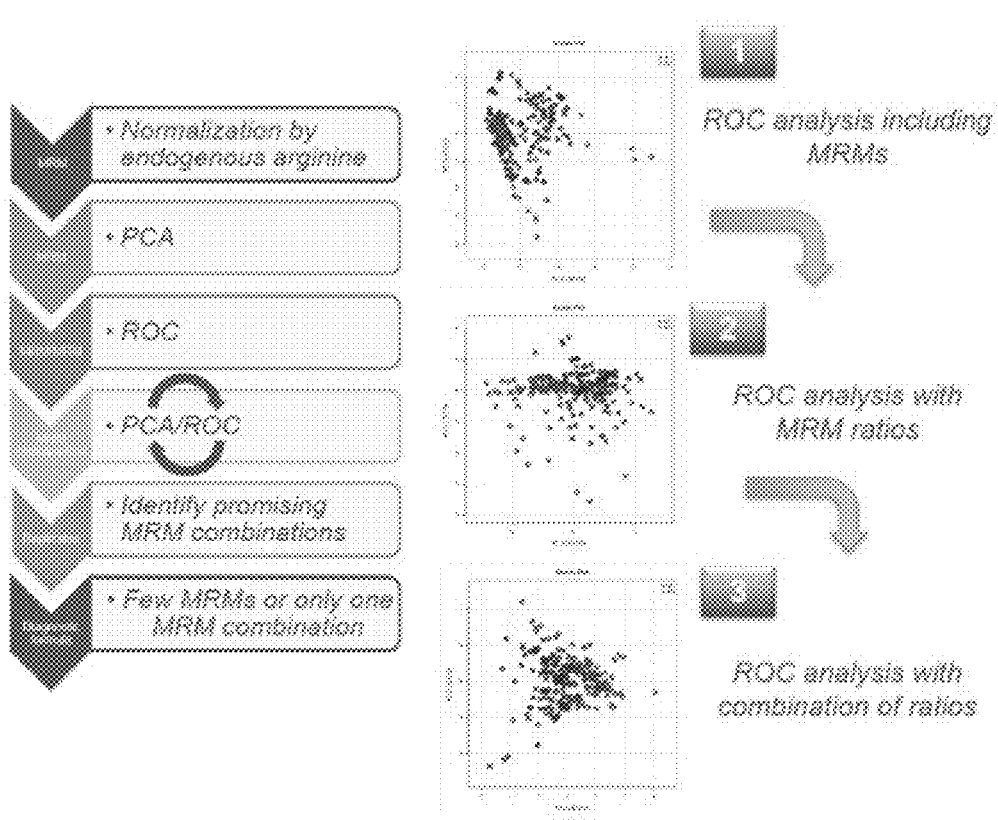
FIG. 1 shows a data analysis workflow overview. MRM ion intensities for each replicate were normalized by the ion intensity of endogenous arginine. The first PCA (indicated by 1) included all the MRM data. Receiver operating characteristic (ROC) analysis guided the selection of the most discriminating MRM and MRM ratios (indicated by 2) MRM ratios were further combined manually based on up and down regulated amounts in PD as well as on pathway analysis, resulting in MRM ratios and combinations of ratios with high discriminating power (indicated by 3).

Multivariate statistical methods allow comparisons of samples that consider in addition the relationships existing amongst molecules. These methods for biomarker discovery are likely to be powerful, since the biological role of a particular factor (such as a pathology or a drug) is usually the result of a series of different mechanisms which are not independent of each other.

Ambient ionization MS refers to the generation of ions under ambient conditions (e.g. pressure, temperature, humidity) while requiring little and in some cases no sample preparation. The ability to examine the sample with minimal preparation (e.g., using only simple dilution) and to do so very rapidly is highly advantageous. Ambient ionization MS has been successful in discriminating between diseased and healthy samples based on patterns of ion intensities. These signals must be reproducible for this approach to be useful but they need not be related directly to the concentrations of specific compounds.

The simplicity of acquisition of full mass scan profiles when using ambient ionization and their successful application to brain cancer diagnosis guided us in developing multiple reaction monitoring (MRM) profiling MS. The discovery phase of the MRM-profiling seeks molecular features based on some prior knowledge of the chemical functional groups likely to be present in the sample. It does this through use of a limited number of pre-chosen and chemically specific neutral loss and/or precursor ion MS/MS scans. The output of the discovery phase is a set of precursor/product transitions. In the screening phase these MRM transitions are used to interrogate multiple samples (hence the name MRM-profiling). MRM profiling is further described for example in Cordeiro et al. (Rapid Commun Mass Spectrom. 2017), the content of which is incorporated by reference herein in its entirety.

Metabolomics guided by functional group recognition, is an approach which we term multiple reaction monitoring (MRM)-profiling, uses specific metabolite fragmentations related to functional groups and classes to interrogate the metabolome. While individual metabolites occur in the many thousands, functional group numbers are roughly 1,000 times lower. This fact results in the much reduced size of MRM-profiling data and in the time needed for analyses using this chemically-assisted profiling of the cellular metabolome. MRM-profiling gives ~$10^3$ less data and requires at least 10 less instrument time than conventional methods since it is intended to cover just the informative part of the data space where metabolites may occur.

Another distinctive feature of MRM-profiling is that it is a 2-step method. MRM-profiling does not look for functional groups in all samples of a study. Instead, in the first step (discovery) only one representative sample of each experimental group, such as a pooled sample, is interrogated. In the second screening step of MRM-profiling, the entire sample set is interrogated but only for ion pairs detected in the discovery step. Multiple reaction monitoring (MRM) measurements are extremely fast (no mass scanning) and their profiles are used for statistical differentiation of the sample types. In other words, the samples are individually interrogated only for the ion pairs that the representative samples have shown to be characteristic of each class.

Figure 4:
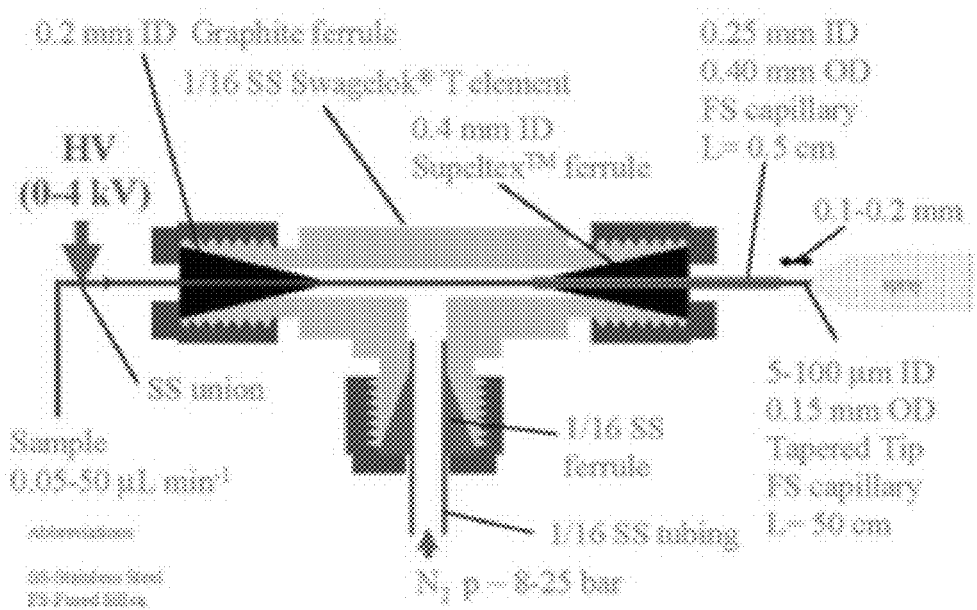
FIG. 4 is an illustration of the ESSI source with dimensional details of its parts.
Figure 5A:
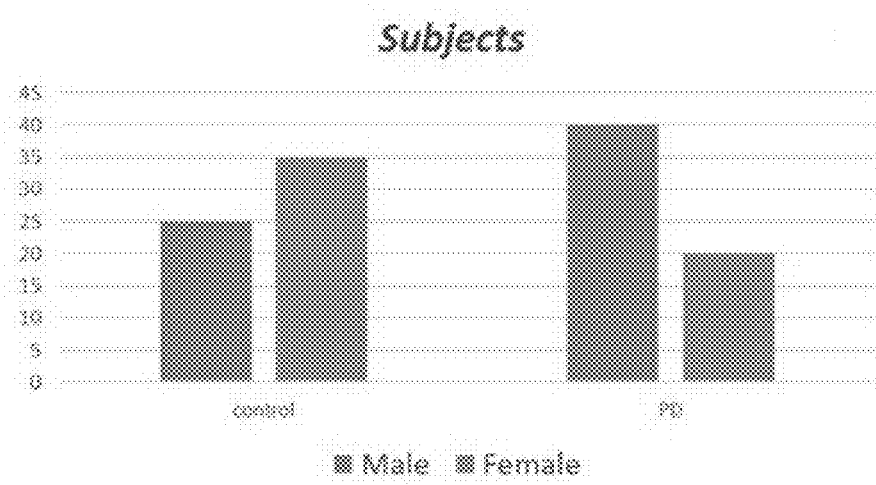
FIGS. 5A-D show distribution of the 120 BioFIND samples according to (FIG. 5A) gender, (FIG. 5B) years of PD diagnosis at CSF collection, (FIG. 5C) Age at CSF collection.
Figure 5B:
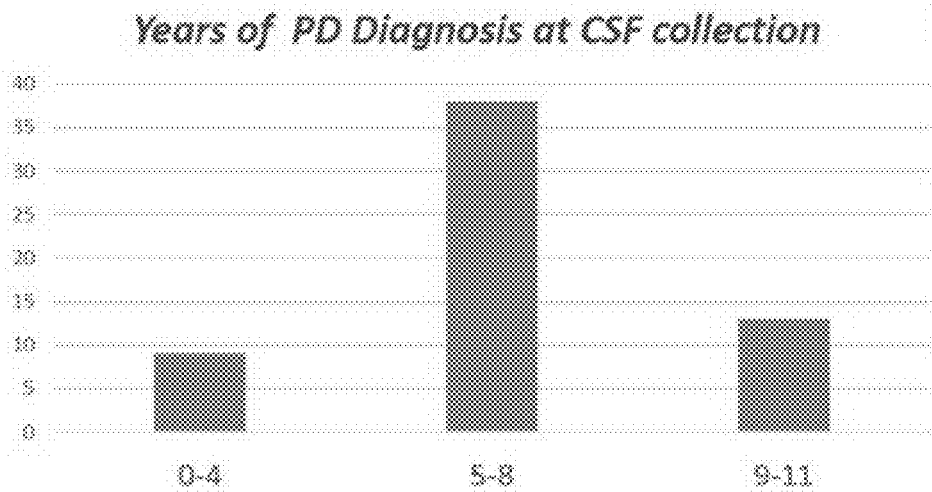
Figure 5C:
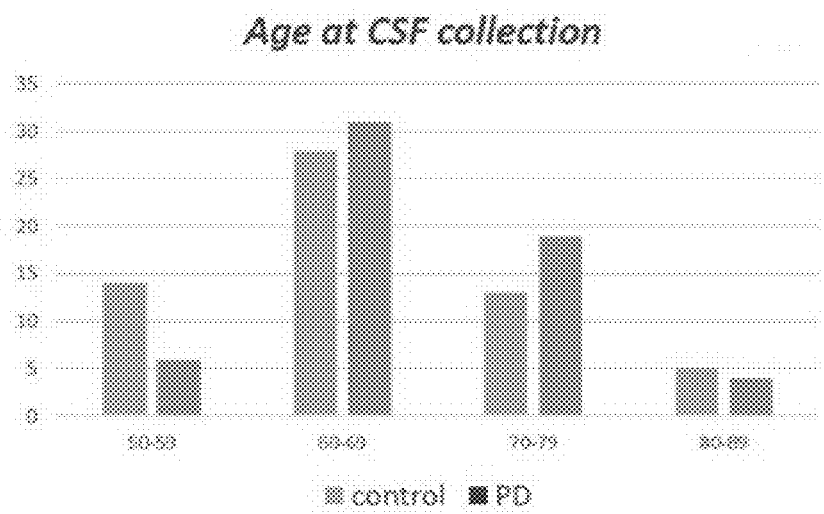
Figure 5D:
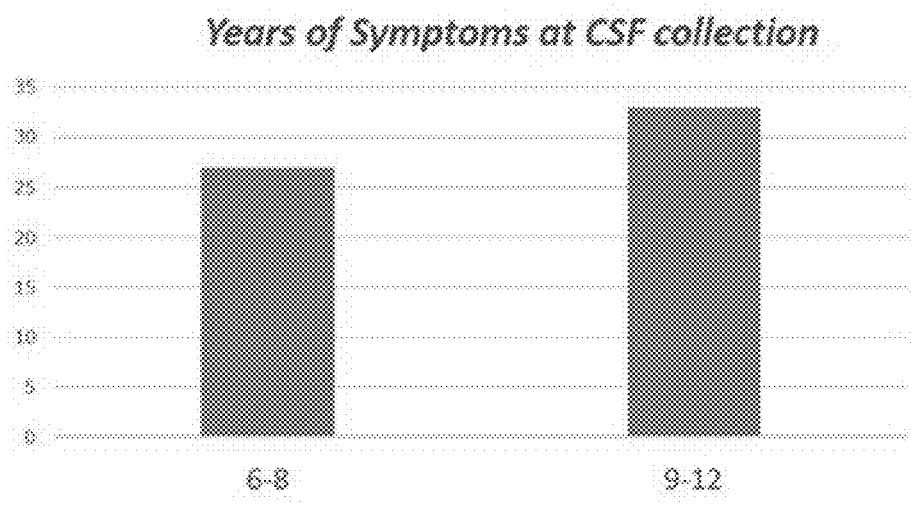
Figure 5E:
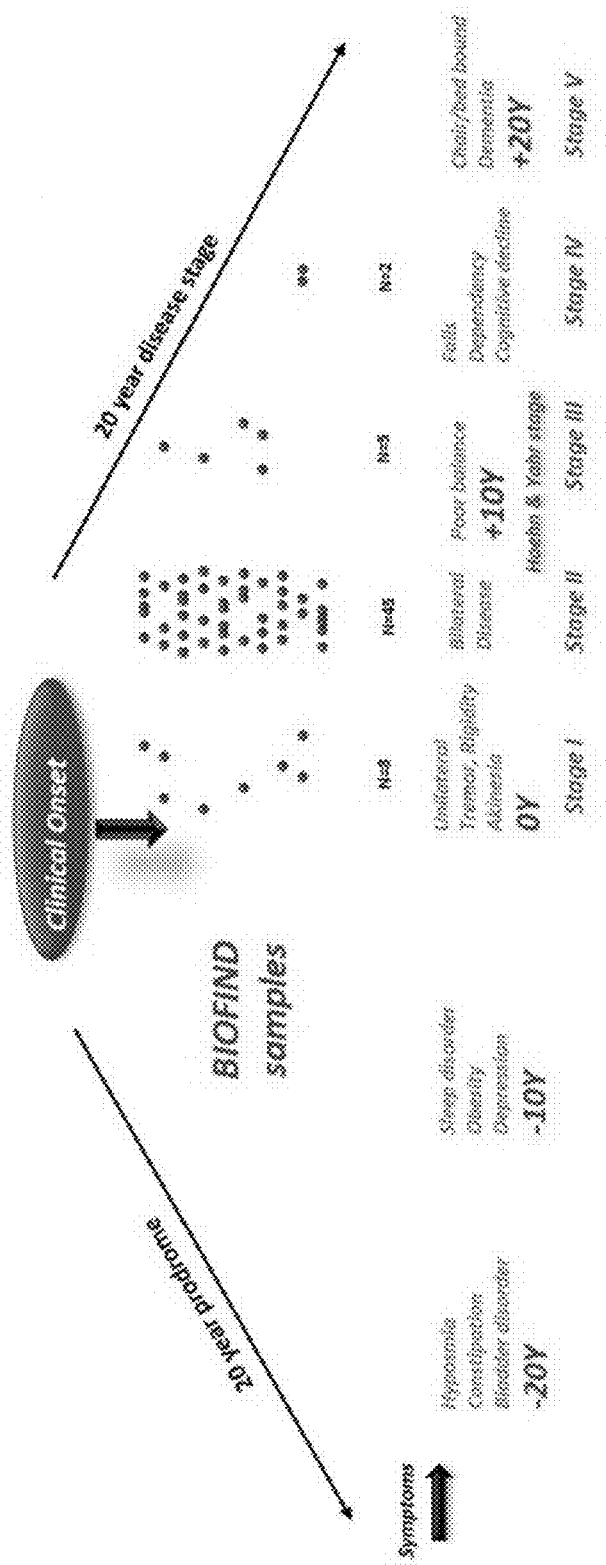
FIG. 5E shows distribution of BioFIND PD samples (dark dots, N=60) according to the Hoehn & Yahr stage scale. Most of the samples (75%) have been classified as Stage II. This schematics is adapted from Hawkes et al., 2013 to illustrate the complexity of PD. Prior to the motor phase of classical PD there is a prodromal period spanning several years. Typical motor features appear in the initial clinical phase and the disease progresses up to 20 years with clinical sign heterogeneity.

Our studies have included the ambient ionization method of paper spray and also electrosonic spray ionization (ESSI). ESSI differs from traditional electrospray ionization (ESI) in using a supersonic nebulizing gas, which generates initial droplets of small sizes, resulting in high desolvation efficiency (FIG. 4). ESSI allows efficient nebulization and tolerates high rates of sample delivery. The samples are not submitted to chromatographic separation but the MRM tandem mass spectrometry experiment provides the needed molecular specificity for chemical profiling. For the MRM experiment, collision induced dissociation (CID) is used to cause fragmentation of an ion mass selected using the first quadrupole with the fragment ion being selected in the third quadrupole of a triple quadrupole MS.

CSF samples were examined by MRM using a triple quadrupole mass spectrometer set to acquire data on many specific ion pairs (precursor and fragment) within 1-2 min. All measurements were then taken into consideration by applying unsupervised multivariate analysis so that the data represent a sensitive and structurally specific chemical fingerprint of a sample.

The MRM profiling method has been applied to the analysis of CSF from PD and two types of control samples, namely clinical controls (CC; patients presenting neurological issues other than PD) and healthy controls (HC; subjects presenting no neurological condition). PD is the second most common neurodegenerative disorder and its clinical diagnosis is difficult in the early stages of disease, with high risks of misdiagnosis.

Preclinical phase PD is believed to span several years, providing the possibility for early therapeutic intervention and a chance for the development of disease-modifying therapies. Nonetheless, the lack of biomarkers for early diagnosis and monitoring of disease progression represents a major obstacle to the development of disease course-modifying therapies. Some 468 CSF metabolites have been re-reported and most of them occur at low ppm levels. CSF is a salty biofluid (145 mM Na), which makes full scan MS data of unmodified samples by electrospray ionization MS noisy and uninformative.

To perform MRM profiling, minute amounts of CSF (13 μL per experiment) were ionized by ESSI after sample dilution. CSF samples had been collected by lumbar puncture and were free of blood contamination (by red blood cell count and haemoglobin measurement) and inflammatory processes (by white cell count, albumin-, IgG-, IgM- and IgA-ratio and oligoclonal bands). Standard operating procedures have been published. Subjects were diagnosed with PD according to UK Brain Bank Criteria. The 27 samples in which the method was developed were supplied by the Paracelsus-Elena-Klinik (Kassel, Germany). The 120 CSF samples to which the developed method was applied were supplied by the BioFIND repository. Most of the BioFIND PD samples (45 out of 60; 75%) were from patients at the same stage of disease (Hoehn & Yahr stage II). Information on age, gender and year of diagnosis for the BioFIND samples is provided in FIGS. 5A-E. The method included MRMs selected through untargeted neutral loss (NL) and precursor (Prec) ion scans (Table 1) and additionally through targeted MRMs (related to specific metabolites) as reported in the literature for LC-MS/MS analysis. We used the most informative MRMs, MRM ratios and MRM combinations, both targeted and untargeted, for the statistical analysis. The initial data indicate that MRM profiling is a promising approach for exploratory metabolomics studies and biomarker screening since it allows fast chemical profiling of low concentrated metabolites present in biofluids.

The MRM profile method used in these experiments was developed after screening a set of CSF of pooled PD patients (N=17) and clinical controls (CC; i.e. patients who presented neurological issues other than PD; N=10). The two sample pools (PD and CC) were interrogated for MRMs reported in the literature for a number of metabolites and by Prec and NL scans related to functional group substructures in order to find informative MRMs. Selected informative MRMs (N=118) for discriminating PD from CC samples as indicated by PCA of replicates of the two pooled samples, plus the MRM of endogenous and stable isotope labelled arginine. The screening method (Table 2) was applied to analysis, individually, of 120 CSF samples (N=60 PD and N=60 healthy controls—HC) by ESSI. The BioFIND CSF samples were also divided into testing (N=30 PD and N=30 HC) and validation sets (N=30 PD and N=30 HC). Three or four replicates per CSF sample were acquired, resulting in 410 measurements for the 120 samples. It must be emphasized that the method was developed using clinical control (CC) samples, from patients presenting neurological symptoms other than PD, and it was then applied in samples from the BioFIND repository. These latter samples included healthy control (HC) samples, viz. healthy subjects presenting no signs of neurological disease. All statistical analyses were carried out using MetaboAnalyst software.

In the first step of data analysis, values of ion intensities of all MRMs were normalized by the endogenous arginine signal. Endogenous arginine was chosen as an endogenous internal standard due to its approximately constant levels in human CSF even in the presence of PD and other neurodegenerative conditions. Analysis of the test set of samples (N=60) was performed by principal component analysis (PCA) and receiver operating characteristics (ROC) taking the PCA results into consideration after the selection of individual MRMs, MRM ratios and MRM combinations (such as summing the MRMs which change according to the experimental group) guided by the ROC curve. In other words, we used "between" and "among" metabolite ratios to capture information lost in univariate and multivariate analysis; we also manually combined MRMs to generate more informative variables. The data analysis workflow procedure is shown in FIG. 1.

Figure 2:
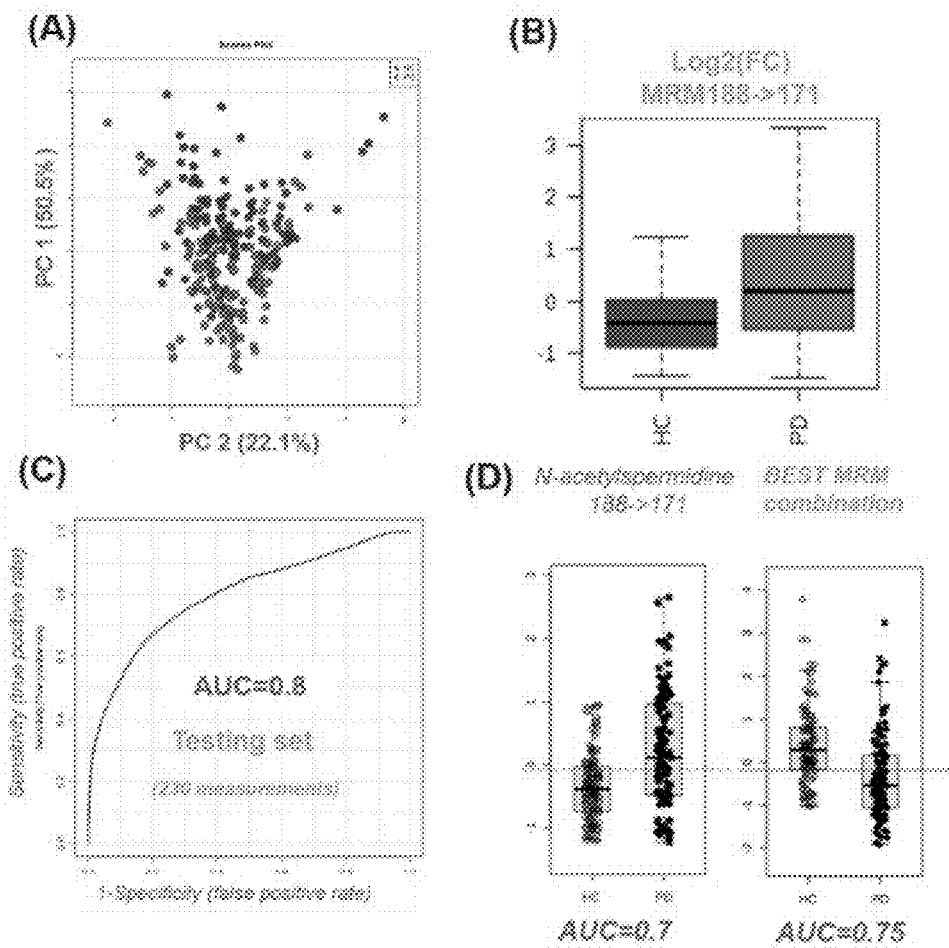
FIG. 2 panels A-D show MRM profiling data from the testing sample set including male and female CSF samples (N=60 subject s, 230 measurements). Data have been normalized to endogenous arginine. Table 2 shows data and CV values among testing set replicates.

Multivariate statistics accounts for the inter-correlation of all molecules and can be highly discriminatory for brain cancer, providing information even on tumor grade and tumor cell concentration. The most informative features for the discrimination of PD from HC in the testing set were used to classify the validation sample set by multivariate ROC analysis. The particular equations resulted from the manual combination of most significant MRMs, but formal methods such as genetic algorithms will be implemented in the future. The PCA with selected variables shows some tendency to discriminate PD (green dots) from HC (red dots) based on the first two PCs (FIG. 2 panel A). The variables used for the multivariate ROC analysis were one MRM consistent with assignment as the polyamine Nacetylspermidine (FIG. 2 panel B) and six other combinations that included nine MRMs (Table 3).

This best MRM combination was the sum of the abundances of four MRMs (134.1→72.4, 177→141.1, 76.2→59.4, and 184→125.2, divided by the abundance of 188→171). The multivariate ROC curve, was built using PLS-DA as the algorithm and the testing set (230 measurements), presented an area under the curve (AUC) value of 0.8 (FIG. 2 panel C). FIG. 2 panel C displays the univariate ROC curve thresholds and the replicate's distribution for the MRM consistent with the assignment as Nacetylspermidine and the best MRM combination found in the HC and PD groups. This ROC curve was used to classify the BioFIND validation set samples (N=60; 180 measurements) and the outcome was that 67% (40 CSF out of 60 samples) were correctly assigned.

Figure 6A:
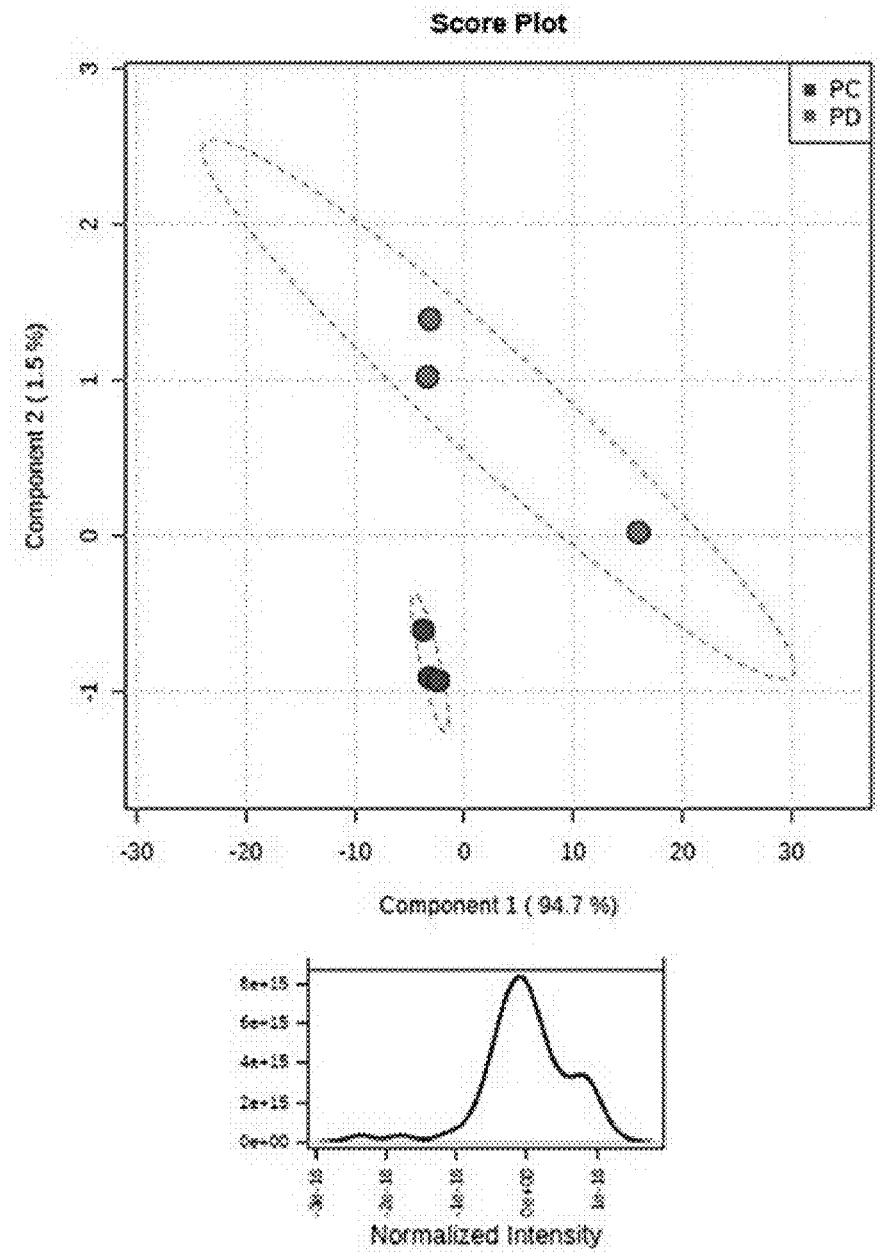
FIGS. 6A-B show that data clinical control (CC) and PD samples (three replicates acquired on three different days) were normalized by (FIG. 6A) the stable isotope of arginine (arginine 13C6 spiked at 50 ppm) and by the (FIG. 6B) endogenous arginine, indicating that endogenous arginine could be used for data normalization.
Figure 6B:
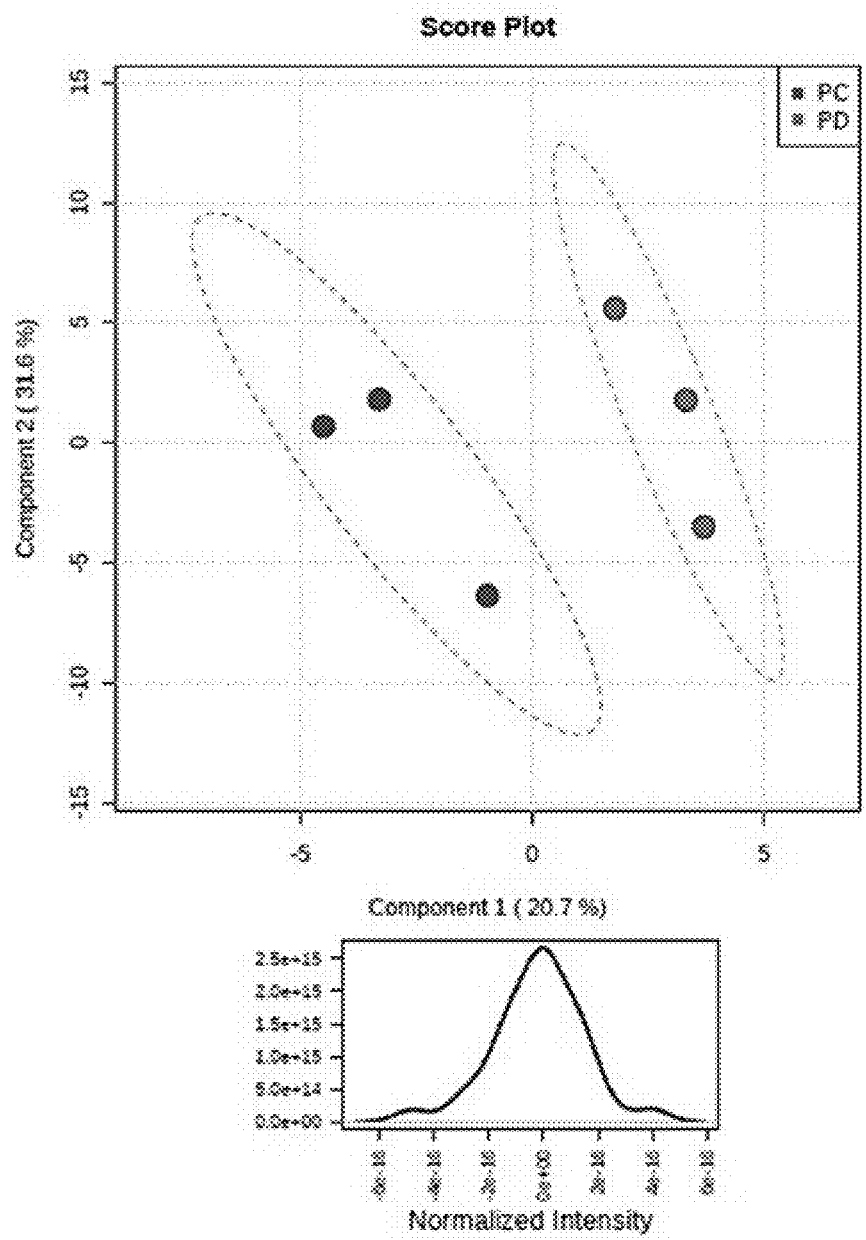
Figure 6C:
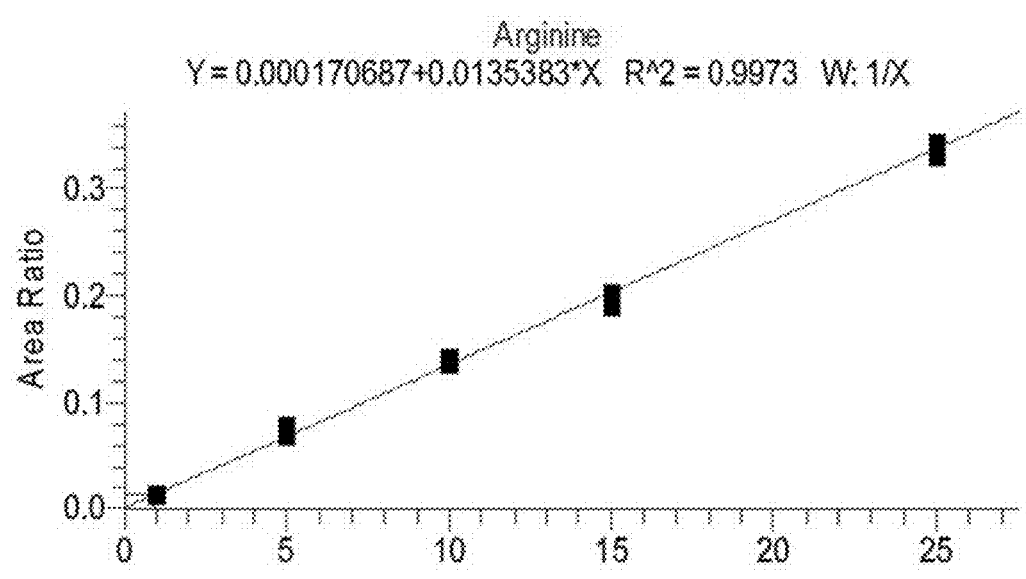
FIG. 6C shows that arginine spiked into artificial CSF showed excellent linear response for quantification in the range 1×-25× (5 replicates for each concentration level) of the physiological concentration (3.5 ppm used as 1× physiological concentration).

When we evaluated diverse co-variates, it was striking that the agreement outcome for males 76% (15 out of 27 samples) was 20% higher than that for the females (56%; 25 out of 33 samples). The ESSI-MRM data (both males and females considered) shows 73.2% sensitivity (82 replicates correctly assigned as PD out of 112) and 70.3% specificity (83 replicates correctly assigned as HC out of 118) as indicated by the confusion matrix of the ROC curve generated with the testing set. No other co-variate besides gender seems to affect the method outcome. A second replicate of this method has been performed with similar results. The underlying approach we have taken to CSF characterization is based on monitoring ion pairs connected by fragmentation. The methodological approach contrasts with strategies using full scan ion abundance profiles (MS profiles) or measurements of the concentrations of individual separated compounds (the standard metabolomics approach). The MRM profiling approach was needed because of their low ppm concentrations of most metabolites in CSF and its high sodium content, which make the full scan mass spectra uninformative. MRM requires prior specification of ions of interest. These specified transitions could be measured together with internal standards for each compound to obtain concentrations of the compounds corresponding to each ion in cases where only a single compound contributes, which is likely to be rare in these very complex mixtures. Hence we use only a single calibrator, the endogenous arginine (physiological average concentration in subjects >18 years old is reported to be 1.6-4.3 ppm), as a 'housekeeping metabolite' and obtain a set of ion intensities that is reproducible and characteristic of the sample, although not directly proportional to the concentrations of individual constituents (FIGS. 6A-C).

MRM profiling introduces one level of chemical specificity to the profiling by monitoring specific ion pairs. The data show that for the MRM of 188→171, which when used alone, presented AUC of 0.7, and which is tentatively assigned to N8- or N1-acetylspermidine. These compounds are polyamines with nervous system activity and they have been suggested to be involved in PD pathogenesis. In particular, N8-acetylspermidine was found to be significantly elevated in the serum of rapid PD progressors compared to both control subjects and slow progressors.

To a lesser extent, but similarly to full profile analysis and direct injection MS approaches, it can be expected that more than one metabolite can be present in the same MRM due to isobaric and isomeric contributions.

It is clear from the initial outcome of MRM profile analysis that the correct classification of subjects as HC and PD is a suitable method for screening biological samples. We are improving the method by changing the experimental design to mirror disease complexity (such as patient stratification by disease stage, medication, and gender). In summary, MRM profiling has promise as a suitable tool for further exploration in PD diagnosis.

We report a first exploration of ambient MRM profiling as an analytical methodology for accelerated biomarker discovery. This strategy has been applied initially to the chemical profiling of CSF, a biofluid with high sodium content and metabolites present at low ppm concentrations. Chemical profiles from a complex disease, PD, for which no validated biomarkers are currently available, showed success for the discrimination of PD from HC samples. The role of N-acetylspermidine as the possible identity of the most informative MRM is discussed. MRM profiling can be useful to other biomarker screening and chemical profiling studies carried out in biofluids and solid samples extracts.

Multiple Reaction Monitoring (MRM)

Figure 7:
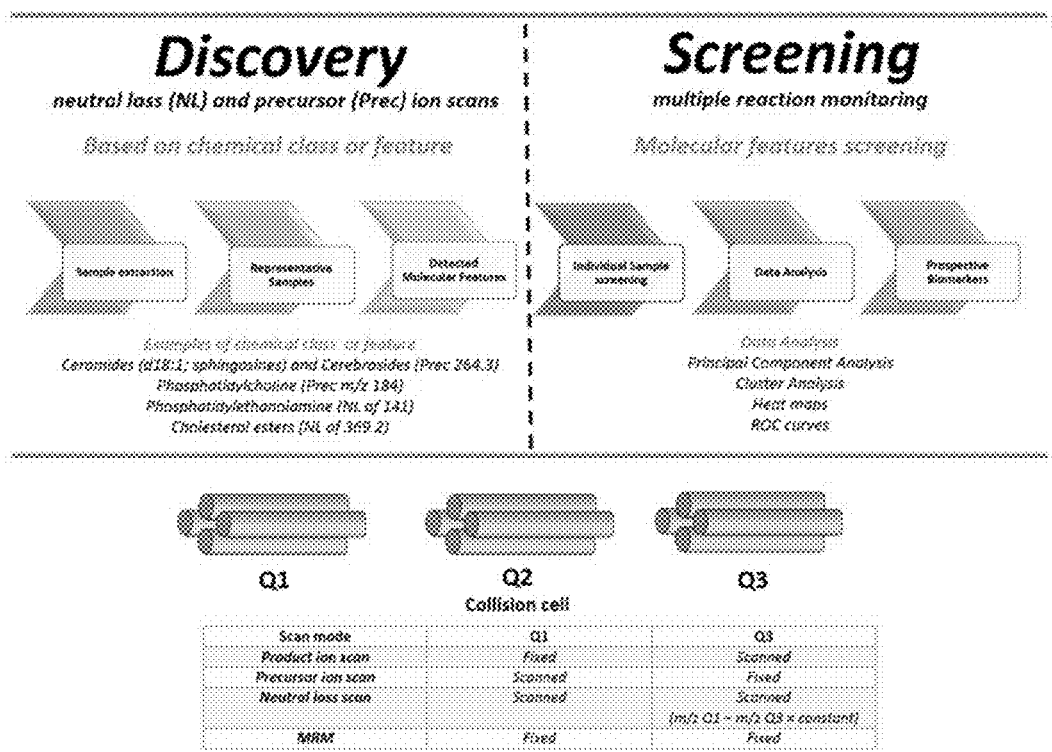
FIG. 7 shows an MRM-Profiling workflow. In the discovery step, sample extracts are directly injected to the ion source of a tandem mass spectrometer, which is set to detect specific chemical classes or chemical features using Precursor (Prec) and Neutral loss (NL) MS/MS scans. Only a small number of representative samples are used in this step. In the screening step, the molecular features detected in the discovery step are organized into precursor/product ion pairs and the fast method of multiple reaction monitoring (MRM) is used to interrogate individual samples. Multivariate statistical analysis then allows sample assignment to particular chemical/biological classes, e.g. diseased/non-diseased. The output of the MRM-profiling method is a panel of discriminant molecular features with the potential to become validated biomarkers. The bottom part of the figure shows the types of scan modes performed (illustrated for the particular case of a triple quadrupole mass spectrometer). Traditional metabolomics approaches are based in product ion scans and they cover most of all of the full 2D-data domain (generating large and complicated datasets). The discovery step of MRM-profiling is based on precursor ion and neutral loss scan (1D-domain) guided by chemical rationale followed by rapid screening using multiple reaction monitoring (zero domain), yielding simpler datasets rich in meaningful molecular information.

Multiple reaction monitoring (MRM)-profiling is a novel mass spectrometric method for accelerated discovery of molecular features, described further in Ferreira et al., (Analyst. 2016 Sep. 21; 141(18):5252-5), the content of which is incorporated by reference herein in its entirety. This method is useful as it allows relative quantification of hundreds of molecules in complex samples. MRM-profiling is characterized by its speed, the absence of chromatographic separation and 'big data' acquisition and reduction. The workflow involves separate discovery and screening steps (FIG. 7).

MRM-profiling is fast and simple because (i) chromatography is not performed, i.e. samples are directly injected into the mass spectrometer ionization source, and (ii) discovery of molecules present in the sample is based on a limited number of chemically specific neutral loss and/or precursor ion MS/MS scans and (iii) no internal standards are used. The discovery step is a supervised method based on chemical inputs based on some prior knowledge of the chemical functional groups likely present in the sample. Prec and NL scans are chemical functional class specific in contrast to product ion MS/MS scans which are specific to particular individual chemical compounds. Traditional metabolic screens record product ion spectra of all the abundant fragment ions in the single stage mass spectrum.

The output of the discovery phase is organized into fast methods for interrogating multiple samples based MRM measurements (hence the name MRM-profiling). Multivariate statistical approaches are performed on the resulting data. MRM-profiling is useful inter alia for healthy/disease discrimination based on small molecules, for better understanding and characterizing gene knockout models, and for observation of dynamic metabolic states (such as the impact of a specific diet).

In more technical detail, for the discovery step of the MRM-profiling, molecules present in representative samples (usually one sample per experimental group) are detected by a molecular feature specific of their chemical class. To detect specific molecular features, a triple quadrupole mass spectrometer (or other tandem instrument) is set to run different experiments looking for fragmentation features related to specific chemical classes using the Prec and NL scan modes. Traditional metabolomics discovery methods are based on product ion scans, which are typically performed over the entire mass range creating of huge dataset (the 2D-data domain) containing all ions detected in the full scan mode and all of their respective fragments. As an example, membrane lipids from the phosphotidylcholine (PC) class have a choline headgroup. When lipids from this class are fragmented, a fragment ion characteristic of PC occurs at mass-to-charge ratio (m/z) 184. Therefore instead of looking at thousands of mass spectra for molecules that might include the fragment of m/z 184, the precursor ion scan shows only molecules having this fragment. For the screening step, molecular features detected in the discovery step (usually hundreds of them) are organized into tailored methods and used to interrogate all samples of interest by MRM scans. Diverse multivariate statistical methods (principal component analysis, cluster analysis) as well as univariate methods (t-test or ANOVA, fold-change, Volcano plot) are used to interrogate the data. Data visualization is by heat maps and methods recommended for biomarker discovery such as receiver operating characteristic (ROC) curves are also used. Even though simpler, chemically broader, and faster than LC-based discovery metabolomics, MRM-profiling allows sample complexity to be preserved during analysis, a feature that is in line with systems biology approaches where a single molecule is rarely enough for the diagnosis or for understanding metabolic conditions.

Training Data Set and Analysis

As discussed above, aspects of the invention involve a database of reference multidimensional chemical profiles, in which each reference multidimensional chemical profile is produced from a training set of data. Any appropriate pattern recognition method (such as those described herein) can be used to develop each reference multidimensional chemical profile and the work herein is based on using training data from a plurality of patients having the specific disease type to be assessed for whom multidimensional chemical profiles and prognosis outcomes are known (the training population). The training data comprise for each patient in the training population (a) a known marker profile; and (b) prognosis outcome information (i.e., disease stage and severity and levels of each chemical in the chemical profile for such disease stage and severity). The markers in the multidimensional chemical profile are selected based on their ability to discriminate prognosis of a disease in a plurality of patients for whom the prognosis outcomes are known. Various methods can be used to evaluate the correlation between marker levels and prognosis. In a preferred embodiment, the training population comprises patients from each of the different stages of a disease.

In preferred embodiments, classification (pattern recognition) methods, e.g., principal component analysis, logic regression, linear or quadratic discriminant analysis, decision trees, clustering, nearest neighbor classifier analysis are applied to the training set of data to generate the data base of reference multidimensional chemical profiles. Such prognosis predictors can be trained with the training population using methods described herein.

In other embodiment, an artificial neural network (ANN) is applied to the training set of data to generate the data base of reference multidimensional chemical profiles. An ANN can be trained with the training population using any suitable method known in the art, e.g., a method described herein. In a specific embodiment, the ANN is a feed-forward back-propagation neural network with a single hidden layer of 10 units, a learning rate of 0.05, and a momentum of 0.2.

In another embodiment, a support vector machine (SVM) is applied to the training set of data to generate the data base of reference multidimensional chemical profiles. In a specific embodiment, the SVM is a linear SVM having a dot product kernel. In still another specific embodiment, the SVM is a nonlinear SVM having a nonlinear kernel, e.g., a d-degree dot product kernel or a Gaussian kernel. An SVM can be trained with the training population using any suitable method known in the art, e.g., a method described herein. Kernels that can be used in conjunction with the present invention are also described.

Other analysis methods that can be applied to the training set of data to obtain the data base of reference multidimensional chemical profiles are described for example in Yeatman et al. (U.S. patent application publication number 2006/0195269), the content of which is incorporated by reference herein in its entirety.

In particular embodiments, principal component analysis (PCA) is applied to the training set of data to obtain the data base of reference multidimensional chemical profiles. Principal component analysis is a classical technique to reduce the dimensionality of a data set by transforming the data to a new set of variable (principal components) that summarize the features of the data. See, for example, Jolliffe, 1986, Principal Component Analysis, Springer, New York. Principal components (PCs) are uncorrelate and are ordered such that the $k^{th}$ PC has the $k^{th}$ largest variance among PCs. The $k^{th}$ PC can be interpreted as the direction that maximizes the variation of the projections of the data points such that it is orthogonal to the first $k-1$ PCs. The first few PCs capture most of the variation in the data set. In contrast, the last few PCs are often assumed to capture only the residual 'noise' in the data.

PCA can also be applied to the training population. In such an approach, vectors for a selected set of molecular markers, specific transitions connecting one or more ion pairs, can be constructed. In fact, the set of vectors, where each vector represents specific transitions connecting one or more ion pairs from a particular member of the training population, can be considered a matrix. In some embodiments, this matrix is represented in a Free-Wilson method of qualitative binary description of monomers (Kubinyi, 1990, 3D QSAR in drug design theory methods and applications, Pergamon Press, Oxford, pp 589-638), and distributed in a maximally compressed space using PCA so that the first principal component (PC) captures the largest amount of variance information possible, the second principal component (PC) captures the second largest amount of all variance information, and so forth until all variance information in the matrix has been accounted for.

Then, each of the vectors (where each vector represents a member of the training population) is plotted. Many different types of plots are possible. In some embodiments, a one-dimensional plot is made. In this one-dimensional plot, the value for the first principal component from each of the members of the training population is plotted. In this form of plot, the expectation is that members of a first group will cluster in one range of first principal component values and members of a second group will cluster in a second range of first principal component values.

In one example, the training population comprises two groups: good prognosis patients and poor prognosis patients. The first principal component is computed using the molecular marker profile across the entire training population data set. Then, each member of the training set is plotted as a function of the value for the first principal component. In this example, those members of the training population in which the first principal component is positive are the good prognosis patients and those members of the training population in which the first principal component is negative are poor prognosis patients.

In some embodiments, the members of the training population are plotted against more than one principal component. For example, in some embodiments, the members of the training population are plotted on a two-dimensional plot in which the first dimension is the first principal component and the second dimension is the second principal component. In such a two-dimensional plot, the expectation is that members of each subgroup represented in the training population will cluster into discrete groups. For example, a first cluster of members in the two-dimensional plot will represent subjects with a mild form of a disease, a second cluster of members in the two-dimensional plot will represent subjects with a moderate form of the disease, and so forth.

In some embodiments, the members of the training population are plotted against more than two principal components and a determination is made as to whether the members of the training population are clustering into groups that each uniquely represents a subgroup found in the training population. In some embodiments, principal component analysis is performed by using the R mva package (Anderson, 1973, Cluster Analysis for applications, Academic Press, New York 1973; Gordon, Classification, Second Edition, Chapman and Hall, CRC, 1999.). Principal component analysis is further described in Duda, Pattern Classification, Second Edition, 2001, John Wiley & Sons, Inc.

In certain embodiments PCA is combined or with receiver operating characteristic (ROC) curve analysis. Such methodology is described for example in Nikas et al. (Am J Transl Res. 2011 Feb. 15; 3(2): 180-196), the content of which is incorporated by reference herein in its entirety. Briefly, all of the variables of the original dataset are assessed in terms of their discriminating power between the target and the reference group (ROC AUC). Those variables with an AUC>θ1 (recommended θ1=0.75) are used in the 1st PCA setting. The classification results of the 1st PCA setting with respect to the original subjects according to the equation of the first principal component (PC1) are recorded, and both the sum and the mean value of the squared residuals of every original subject as predicted by PC1 (Q1) are calculated. Those variables with an AUC>θ1 (recommended θ1=0.80) are used in the 2nd PCA setting. The classification results of the 2nd PCA setting with respect to the original subjects according to the equation of the first principal component (PC1) are recorded, and both the sum and the mean value of the squared residuals Q1 are calculated. The previous two steps are repeated k times with increasing AUC values until the kth PCA setting, wherein only those original variables with an AUC>θk are used, yields a) the most accurate classification results with respect to the original subjects and b) the smallest mean value and sum value of all Q1 squared residuals. This kth PCA setting constitutes the diagnostic model. The diagnostic model can then be tested with unknown subjects.

As is clear for the examples herein, the type of disease is not critical and the techniques describes herein can be applied to any disease because the training population includes known known outcomes. The techniques described herein can be iteratively applied to the training population to thus identify promising MRM combinations, which are then mapped back to the members of the training population and cross-references to the disease stage for that member of the population. In that manner, a reference database of multi-dimensional chemical profiles is then created for any disease. Each reference multidimensional chemical profile in the database has been produced from the training set of data, so each reference multidimensional chemical profile is associated with an individual having a particular stage of the disease as well as a known multidimensional chemical profile that is correlated to that stage of the disease.

Ion Generation

Any approach for generating ions known in the art may be employed. Exemplary mass spectrometry techniques that utilize ionization sources at atmospheric pressure for mass spectrometry include electrospray ionization (ESI; Fenn et al., Science, 246:64-71, 1989; and Yamashita et al., J. Phys. Chem., 88:4451-4459, 1984); atmospheric pressure ionization (APCI; Carroll et al., Anal. Chem. 47:2369-2373, 1975); and atmospheric pressure matrix assisted laser desorption ionization (AP-MALDI; Laiko et al. Anal. Chem., 72:652-657, 2000; and Tanaka et al. Rapid Commun. Mass Spectrom., 2:151-153, 1988). The content of each of these references in incorporated by reference herein in its entirety.

Exemplary mass spectrometry techniques that utilize direct ambient ionization/sampling methods including desorption electrospray ionization (DESI; Takats et al., Science, 306:471-473, 2004 and U.S. Pat. No. 7,335,897); direct analysis in real time (DART; Cody et al., Anal. Chem., 77:2297-2302, 2005); Atmospheric Pressure Dielectric Barrier Discharge Ionization (DBDI; Kogelschatz, Plasma Chemistry and Plasma Processing, 23:1-46, 2003, and PCT international publication number WO 2009/102766), ion generation using a wetted porous material (Paper Spray, U.S. Pat. No. 8,859,956), and electrospray-assisted laser desorption/ionization (ELDI; Shiea et al., J. Rapid Communications in Mass Spectrometry, 19:3701-3704, 2005). The content of each of these references in incorporated by reference herein its entirety.

Ion generation can be accomplished by placing the sample on a porous material and generating ions of the sample from the porous material or other type of surface, such as shown in Ouyang et al., U.S. Pat. No. 8,859,956, the content of which is incorporated by reference herein in its entirety. Alternatively, the assay can be conducted and ions generated from a non-porous material, see for example, Cooks et al., U.S. patent application Ser. No. 14/209,304, the content of which is incorporated by reference herein in its entirety). In certain embodiments, a solid needle probe or surface to which a high voltage may be applied is used for generating ions of the sample (see for example, Cooks et al., U.S. patent application publication number 20140264004, the content of which is incorporated by reference herein in its entirety).

In certain embodiments, ions of a sample are generated using nanospray ESI. Exemplary nano spray tips and methods of preparing such tips are described for example in Wilm et al. (Anal. Chem. 2004, 76, 1165-1174), the content of which is incorporated by reference herein in its entirety. NanoESI is described for example in Karas et al. (Fresenius J Anal Chem. 2000 March-April; 366(6-7):669-76), the content of which is incorporated by reference herein in its entirety.

In preferred embodiments, electrosonic spray ionization (ESSI) is employed to ionizes a sample. ESSI is described for example in Takats eta l. (Anal. Chem., 2004, 76 (14), pp 4050-4058), the content of which is incorporated by reference herein in its entirety. Electrosonic spray ionization (ESSI), a variant on electrospray ionization (ESI), employs a traditional micro ESI source with supersonic nebulizing gas. The high linear velocity of the nebulizing gas provides efficient pneumatic spraying of the charged liquid sample. The variable electrostatic potential can be tuned to allow efficient and gentle ionization.

Mass Spectrometers and Ion Traps

Any mass spectrometer (e.g., bench-top mass spectrometer of miniature mass spectrometer) may be used in systems of the invention and in certain embodiments the mass spectrometer is a miniature mass spectrometer. An exemplary miniature mass spectrometer is described, for example in Gao et al. (Anal. Chem. 2008, 80, 7198-7205.), the content of which is incorporated by reference herein in its entirety. In comparison with the pumping system used for lab-scale instruments with thousands of watts of power, miniature mass spectrometers generally have smaller pumping systems, such as a 18 W pumping system with only a 5 L/min (0.3 m$^3$/hr) diaphragm pump and a 11 L/s turbo pump for the system described in Gao et al. Other exemplary miniature mass spectrometers are described for example in Gao et al. (Anal. Chem., 2008, 80, 7198-7205.), Hou et al. (Anal. Chem., 2011, 83, 1857-1861.), PCT/US17/26269 to Purdue Research Foundation, and Sokol et al. (Int. J. Mass Spectrom., 2011, 306, 187-195), the content of each of which is incorporated herein by reference in its entirety.

Any ion trap known in the art can be used in systems of the invention. Exemplary ion traps include a hyperbolic ion trap (e.g., U.S. Pat. No. 5,644,131, the content of which is incorporated by reference herein in its entirety), a cylindrical ion trap (e.g., Bonner et al., International Journal of Mass Spectrometry and Ion Physics, 24(3):255-269, 1977, the content of which is incorporated by reference herein in its entirety), a linear ion trap (Hagar, Rapid Communications in Mass Spectrometry, 16(6):512-526, 2002, the content of which is incorporated by reference herein in its entirety), and a rectilinear ion trap (U.S. Pat. No. 6,838,666, the content of which is incorporated by reference herein in its entirety).

System Architecture

The methods of the invention can be carried out and embodied in certain systems. Accordingly, the invention also provides systems for MRM profiling. Such systems may include a mass spectrometer suitable for performing MRM, such as a triple quadrupole mass spectrometer, an ionizing source (such as an ambient ionization source as discussed herein), and a data analysis module, e.g., a computer, all operably connected to each other.

Aspects of the invention described herein can be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. For example, the reference set of data may be stored at a remote location and the computer communicates across a network to access the reference set to compare data derived from the female subject to the reference set. In other embodiments, however, the reference set is stored locally within the computer and the computer accesses the reference set within the CPU to compare subject data to the reference set. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

Figure 3:
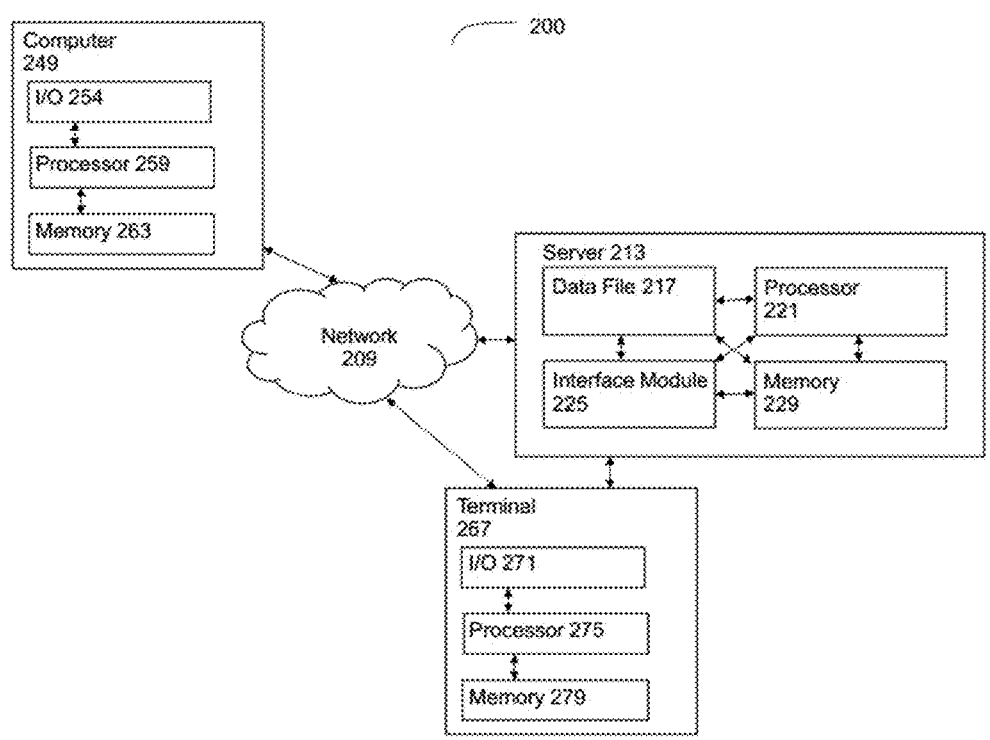
FIG. 3 is an illustration showing an exemplary data analysis module for implementing the methods of the invention.

In an exemplary embodiment shown in FIG. 3, system 200 can include a computer 249 (e.g., laptop, desktop, or tablet). The computer 249 may be configured to communicate across a network 209. Computer 249 includes one or more processor 259 and memory 263 as well as an input/output mechanism 254. Where methods of the invention employ a client/server architecture, an steps of methods of the invention may be performed using server 213, which includes one or more of processor 221 and memory 229, capable of obtaining data, instructions, etc., or providing results via interface module 225 or providing results as a file 217. Server 213 may be engaged over network 209 through computer 249 or terminal 267, or server 213 may be directly connected to terminal 267, including one or more processor 275 and memory 279, as well as input/output mechanism 271.

System 200 or machines according to the invention may further include, for any of I/O 249, 237, or 271 a video display unit (e.g., a liquid crystal display (LCD) or a cathode ray tube (CRT)). Computer systems or machines according to the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 263, 279, or 229 according to the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

Exemplary step-by-step methods are now described. It will be understood that of the methods described herein, as well as any portion of the systems and methods disclosed herein, can be implemented by computer, including the devices described above. A biological sample is ionized using an ionizing source and the ionized sample is sent into a mass spectrometer. Mass spectrometry data is generated using multiple reaction monitoring of specific ion pairs in the mass spectrometer. That data is then sent to the central processing unit (CPU) of a computer, i.e., the computer receives the mass spectrometry data of the biological sample obtained by multiple reaction monitoring. The mass spectrometry data includes specific transitions connecting one or more ion pairs within the sample.

The CPU is coupled to a storage or memory for storing instructions for implementing methods of the present invention. The instructions, when executed by the CPU, cause the CPU to apply an unsupervised multivariate analysis to the mass spectrometry data in order to generate a multidimensional chemical profile of the sample. The CPU is then caused to compare the multidimensional chemical profile of the sample to a database of reference multidimensional chemical profiles, wherein each reference multidimensional chemical profile is produced from a training set of data from a population of patients with a known disease status, thereby screening the biological sample. The reference set of data may be stored locally within the computer, such as within the computer memory. Alternatively, the reference set may be stored in a location that is remote from the computer, such as a server. In this instance, the computer communicates across a network to access the reference set of data.

Samples

The systems and methods of the invention can be used to analyze many different types of samples. A wide range of heterogeneous samples can be analyzed, such as biological samples, environmental samples (including, e.g., industrial samples and agricultural samples), and food/beverage product samples, etc.).

Exemplary environmental samples include, but are not limited to, groundwater, surface water, saturated soil water, unsaturated soil water; industrialized processes such as waste water, cooling water; chemicals used in a process, chemical reactions in an industrial processes, and other systems that would involve leachate from waste sites; waste and water injection processes; liquids in or leak detection around storage tanks; discharge water from industrial facilities, water treatment plants or facilities; drainage and leachates from agricultural lands, drainage from urban land uses such as surface, subsurface, and sewer systems; waters from waste treatment technologies; and drainage from mineral extraction or other processes that extract natural resources such as oil production and in situ energy production.

Additionally exemplary environmental samples include, but certainly are not limited to, agricultural samples such as crop samples, such as grain and forage products, such as soybeans, wheat, and corn. Often, data on the constituents of the products, such as moisture, protein, oil, starch, amino acids, extractable starch, density, test weight, digestibility, cell wall content, and any other constituents or properties that are of commercial value is desired.

Exemplary biological samples include a human tissue or bodily fluid and may be collected in any clinically acceptable manner. A tissue is a mass of connected cells and/or extracellular matrix material, e.g. skin tissue, hair, nails, nasal passage tissue, CNS tissue, neural tissue, eye tissue, liver tissue, kidney tissue, placental tissue, mammary gland tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sputum, sweat, amniotic fluid, menstrual fluid, mammary fluid, peritoneal fluid, urine, semen, and cerebrospinal fluid (CSF), such as lumbar or ventricular CSF. A sample may also be a fine needle aspirate or biopsied tissue. A sample also may be media containing cells or biological material. A sample may also be a blood clot, for example, a blood clot that has been obtained from whole blood after the serum has been removed.

In one embodiment, the biological sample can be a blood sample, from which plasma or serum can be extracted. The blood can be obtained by standard phlebotomy procedures and then separated. Typical separation methods for preparing a plasma sample include centrifugation of the blood sample. For example, immediately following blood draw, protease inhibitors and/or anticoagulants can be added to the blood sample. The tube is then cooled and centrifuged, and can subsequently be placed on ice. The resultant sample is separated into the following components: a clear solution of blood plasma in the upper phase; the buffy coat, which is a thin layer of leukocytes mixed with platelets; and erythrocytes (red blood cells). Typically, 8.5 mL of whole blood will yield about 2.5-3.0 mL of plasma.

Blood serum is prepared in a very similar fashion. Venous blood is collected, followed by mixing of protease inhibitors and coagulant with the blood by inversion. The blood is allowed to clot by standing tubes vertically at room temperature. The blood is then centrifuged, wherein the resultant supernatant is the designated serum. The serum sample should subsequently be placed on ice.

Prior to analyzing a sample, the sample may be purified, for example, using filtration or centrifugation. These techniques can be used, for example, to remove particulates and chemical interference. Various filtration media for removal of particles includes filer paper, such as cellulose and membrane filters, such as regenerated cellulose, cellulose acetate, nylon, PTFE, polypropylene, polyester, polyethersulfone, polycarbonate, and polyvinylpyrolidone. Various filtration media for removal of particulates and matrix interferences includes functionalized membranes, such as ion exchange membranes and affinity membranes; SPE cartridges such as silica- and polymer-based cartridges; and SPE (solid phase extraction) disks, such as PTFE- and fiberglass-based. Some of these filters can be provided in a disk format for loosely placing in filter holdings/housings, others are provided within a disposable tip that can be placed on, for example, standard blood collection tubes, and still others are provided in the form of an array with wells for receiving pipetted samples. Another type of filter includes spin filters. Spin filters consist of polypropylene centrifuge tubes with cellulose acetate filter membranes and are used in conjunction with centrifugation to remove particulates from samples, such as serum and plasma samples, typically diluted in aqueous buffers.

Filtration is affected in part, by porosity values, such that larger porosities filter out only the larger particulates and smaller porosities filtering out both smaller and larger porosities. Typical porosity values for sample filtration are the 0.20 and 0.45 µm porosities. Samples containing colloidal material or a large amount of fine particulates, considerable pressure may be required to force the liquid sample through the filter. Accordingly, for samples such as soil extracts or wastewater, a prefilter or depth filter bed (e.g. "2-in-1" filter) can be used and which is placed on top of the membrane to prevent plugging with samples containing these types of particulates.

In some cases, centrifugation without filters can be used to remove particulates, as is often done with urine samples. For example, the samples are centrifuged. The resultant supernatant is then removed and frozen.

After a sample has been obtained and purified, the sample can be analyzed. With respect to the analysis of a blood plasma sample, there are many elements present in the plasma, such as proteins (e.g., Albumin), ions and metals (e.g., iron), vitamins, hormones, and other elements (e.g., bilirubin and uric acid). Any of these elements may be detected. More particularly, systems of the invention can be used to detect molecules in a biological sample that are indicative of a disease state. Specific examples are provided below.

Where one or more of the target molecules in a sample are part of a cell, the aqueous medium may also comprise a lysing agent for lysing of cells. A lysing agent is a compound or mixture of compounds that disrupt the integrity of the membranes of cells thereby releasing intracellular contents of the cells. Examples of lysing agents include, but are not limited to, non-ionic detergents, anionic detergents, amphoteric detergents, low ionic strength aqueous solutions (hypotonic solutions), bacterial agents, aliphatic aldehydes, and antibodies that cause complement dependent lysis, for example. Various ancillary materials may be present in the dilution medium. All of the materials in the aqueous medium are present in a concentration or amount sufficient to achieve the desired effect or function.

In some examples, where one or more of the target molecules are part of a cell, it may be desirable to fix the cells of the sample. Fixation of the cells immobilizes the cells and preserves cell structure and maintains the cells in a condition that closely resembles the cells in an in vivo-like condition and one in which the antigens of interest are able to be recognized by a specific affinity agent. The amount of fixative employed is that which preserves the cells but does not lead to erroneous results in a subsequent assay. The amount of fixative may depend for example on one or more of the nature of the fixative and the nature of the cells. In some examples, the amount of fixative is about 0.05% to about 0.15% or about 0.05% to about 0.10%, or about 0.10% to about 0.15% by weight. Agents for carrying out fixation of the cells include, but are not limited to, cross-linking agents such as, for example, an aldehyde reagent (such as, e.g., formaldehyde, glutaraldehyde, and paraformaldehyde,); an alcohol (such as, e.g., $C_1$-$C_5$ alcohols such as methanol, ethanol and isopropanol); a ketone (such as a $C_3$-$C_5$ ketone such as acetone); for example. The designations $C_1$-$C_5$ or $C_3$-$C_5$ refer to the number of carbon atoms in the alcohol or ketone. One or more washing steps may be carried out on the fixed cells using a buffered aqueous medium.

If necessary after fixation, the cell preparation may also be subjected to permeabilization. In some instances, a fixation agent such as, an alcohol (e.g., methanol or ethanol) or a ketone (e.g., acetone), also results in permeabilization and no additional permeabilization step is necessary. Permeabilization provides access through the cell membrane to target molecules of interest. The amount of permeabilization agent employed is that which disrupts the cell membrane and permits access to the target molecules. The amount of permeabilization agent depends on one or more of the nature of the permeabilization agent and the nature and amount of the cells. In some examples, the amount of permeabilization agent is about 0.01% to about 10%, or about 0.1% to about 10%. Agents for carrying out permeabilization of the cells include, but are not limited to, an alcohol (such as, e.g., $C_1$-$C_5$ alcohols such as methanol and ethanol); a ketone (such as a $C_3$-$C_5$ ketone such as acetone); a detergent (such as, e.g., saponin, TRITON X-100 (4-(1,1,3,3-Tetramethylbutyl)phenyl-polyethylene glycol, t-Octylphenoxypolyethoxyethanol, Polyethylene glycol tert-octylphenyl ether buffer, commercially available from Sigma Aldrich), and TWEEN-20 (Polysorbate 20, commercially available from Sigma Aldrich)). One or more washing steps may be carried out on the permeabilized cells using a buffered aqueous medium.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Methods and Samples

Methanol was purchased from Avantor Performance Materials (Center Valley, Pa., US), and acetic acid from Mallinckrodt Baker Inc. (Phillipsburg, N.J., US.). Cerebrospinal fluid (CSF) samples (N=10 clinical control and N=17 PD) supplied by Elena-Paracelsus-Klinik (Kassel, Germany) were used for method development.

For electrosonic spray ionization (ESSI) each CSF sample was diluted 16 times with 95% methanol, 5% water and 0.1% acetic acid. This solution was mixed well and injected via syringe into the spray source. ESSI is an ionization methodology that is comparable to electrospray ionization. It utilizes a high velocity nebulizing gas surrounding the sample emitter to rapidly evaporate the charged microdroplets and create gas phase ions. ESSI is a good ionization technique to use in exploratory methodologies because it provides a direct injection of the sample removing any potential interferences from other ionization techniques. The ESSI source (FIG. 4) consists of a sample syringe connected to fused silica line that has a 100 µm inner diameter. This line is inserted through a Swagelock T fitting and allowed to protrude 0.1-0.2 mm to create a spray tip. Nitrogen at 100 psi is injected into the T fitting and serves as the nebulizing gas for the spray by covering the spray tip in a high velocity gas. The spray tip is placed 1 cm away from the mass spectrometer inlet. In this experiment, a high voltage of 3.5 kV was applied to the sample syringe and the sample solution was injected at a flow rate of 3 µL/min. The spray plume was observed to be stable before every sample was run.

A triple quadrupole mass spectrometer (TSQ Quantum Access Max, Thermo Scientific, San Jose, Calif.) operated in the positive ion mode was used for all experiments. The MRM transitions were selected based on exploratory research by neutral loss and precursor ion scan experiments (Table 1) using pooled samples representative of the control and disease groups. Also screening was performed for MRMs reported in the literature. Values of collision energy (CE) and tube lens (TL) were optimized experimentally for each MRM (Table 2).

TABLE 1

Examples of neutral losses and precursor ion scan that can be used to identify informative MRMs.

| Mass units Lost | Ion mode | Scan mode | Related common metabolites |
|---|---|---|---|
| 17 | pos/neg | NL | Amines |
| 18 | pos/neg | NL | Carboxylic Acids, Aldehydes |
| 28 | pos/neg | NL | Aldehydes, Carboxylic Acids |
| 44 | pos/neg | NL | Carboxylic Acids |
| 176 | pos/neg | NL | Glucoronides |
| 162 | pos/neg | NL | Hexose Sugars |
| 132 | pos/neg | NL | Pentose Sugars |
| 80 | pos | NL | Phenolic Sulphates |
| 79 | neg | Prec | Phosphates |
| 124 | neg | Prec | Taurines |
| 129 | neg | NL | N-Acetylcysteines |
| 85 | pos | Prec | Acylcarnitines |

NL = netural loss; Prec = precursor scan

TABLE 2

Ion pairs (precursor and fragment), collision energy (CE) settings for the MRM profiling method, and compound possibly associated with the MRMs based on the HMBD database*#

| Precursor | Fragment | CE | Suggested compound from HMDB precursor mass |
|---|---|---|---|
| 76.2 | 58.3 | 5 | Not attributed |
| 76.2 | 59.4 | 16 | Trimethylamine N-Oxide (HMDB00925) |
| 78.2 | 61.5 | 5 | Cysteamine (HMDB02991) |
| 79.2 | 61.5 | 5 | Dimethyl sulfoxide (HMDB02151) |
| 88.1 | 57.5 | 15 | Pyruvic acid/Putrescine (HMDB00243) |
| 88.1 | 71.3 | 7 | Pyruvic acid/Putrescine (HMDB00243) |
| 113.1 | 59.2 | 20 | Uracil (HMDB00300) |
| 113.1 | 70 | 17 | Uracil (HMDB00300) |
| 113.1 | 77.3 | 14 | Uracil (HMDB00300) |
| 115.1 | 79.2 | 15 | Fumarate/Maleate (HMDB00134) |
| 115.1 | 97.1 | 5 | Fumarate/Maleate (HMDB00134) |
| 116.1 | 70 | 15 | Proline (HMDB00162) |
| 116.1 | 88.2 | 7 | Proline (HMDB00162) |
| 116.1 | 98.1 | 15 | Proline (HMDB00162) |

TABLE 2-continued

Ion pairs (precursor and fragment), collision energy (CE) settings for the MRM profiling method, and compound possibly associated with the MRMs based on the HMBD database*#

| Precursor | Fragment | CE | Suggested compound from HMDB precursor mass |
|---|---|---|---|
| 116.1 | 98.4 | 8 | Proline (HMDB00162) |
| 117.0 | 81.2 | 6 | Not assigned |
| 117.0 | 99.1 | 10 | Not assigned |
| 120.1 | 84 | 14 | L-Threonine (HMDB00167) |
| 120.1 | 102.4 | 5 | L-Threonine (HMDB00167) |
| 122.1 | 68.4 | 25 | L-Cysteine/Nicotinate (HMDB00167) |
| 122.1 | 77.3 | 10 | L-Cysteine/Nicotinate (HMDB00167) |
| 132.1 | 44.5 | 25 | Creatine (HMDB00064) |
| 132.1 | 90.5 | 13 | Creatine/(iso)leucine/4-OH-proline (HMDB00064) |
| 133.0 | 115.3 | 7 | L-asparagine (HMDB00168) |
| 134.1 | 72.4 | 18 | Aspartate (HMDB00191) |
| 134.1 | 115.8 | 5 | Aspartate (HMDB00191) |
| 136.1 | 100.2 | 12 | Homocysteine (HMDB00742) |
| 141.0 | 81.1 | 5 | Methylimidazoleacetic acid (HMDB02820) |
| 141.0 | 83.2 | 6 | Not Assigned |
| 142.1 | 124.2 | 8 | Not Assigned |
| 146.1 | 109.9 | 15 | 4-Guanidinobutanoic acid (HMDB03464) |
| 150.1 | 114.3 | 5 | Not Assigned |
| 151.0 | 115.1 | 9 | L-Threo-2-pentulose (HMDB00751) |
| 151.0 | 83.23 | 18 | L-Threo-2-pentulose/D-Xylulose/Xanthine (HMDB00751) |
| 153.0 | 99.1 | 13 | D-Arabitol/Cystamine (HMDB00568) |
| 153.0 | 135 | 5 | D-Arabitol/Cystamine (HMDB00568) |
| 153.0 | 55.3 | 28 | D-Arabitol/Cystamine (HMDB00568) |
| 154.0 | 136.1 | 5 | 3-Sulfinoalanine/3-OH-anthranilate (HMDB00996) |
| 155.0 | 119.1 | 11 | Orotate (HMD800226) |
| 155.0 | 137.1 | 5 | Orotate (HMD800226) |
| 166.0 | 105.2 | 5 | Quinolinic acid (HMD800232) |
| 166.0 | 103.2 | 28 | Not Assigned |
| 166.1 | 120.2 | 14 | Not Assigned |
| 167.0 | 131.1 | 7 | Not Assigned |
| 168.0 | 149.8 | 6 | Quinolinic acid (HMDB00232) |
| 168.1 | 150.2 | 5 | Quinolinic acid (HMDB00232) |
| 169.0 | 151.1 | 5 | 3,4-Dihydroxybenzeneacetic acid/DHAP (HMD801336) |
| 169.0 | 151.2 | 6 | 3,4-Dihydroxybenzeneacetic acid/DHAP (HMD801336) |
| 169.0 | 115.1 | 18 | 3,4-Dihydroxybenzeneacetic acid/DHAP (HMD801336) |
| 169.2 | 151.2 | 5 | Not Assigned |
| 170.0 | 152.2 | 6 | Not Assigned |
| 171.0 | 134.9 | 5 | Not Assigned |
| 175.0 | 139 | 5 | N-Acetyl-L-aspartic acid (HMD800812) |
| 175.0 | 157.1 | 5 | Suberic acid/N-Acetyl-L-aspartic acid/Ascorbate (HMD800893) |
| 175.1 | 70.3 | 25 | Arginine (HMD800517) |
| 177.0 | 141.1 | 6 | Serotonin (HMD800259) |
| 177.0 | 159.1 | 5 | Serotonin (HMD800259) |
| 177.0 | 159 | 5 | Serotonin (HMD800259) |
| 177.1 | 160 | 12 | Serotonin (HMD800259) |
| 181.2 | 74.3 | 23 | Arginine stable isotope |
| 182.0 | 165.1 | 6 | Hydroxyphenyllactic acid (HMD800755) |
| 182.0 | 91.2 | 30 | Tyrosine (HMD800158) |
| 182.8 | 165.2 | 5 | Homovanillic acid (HMD800118) |
| 183.0 | 164.9 | 6 | Not Assigned |
| 183.0 | 165.1 | 6 | Homovanillic acid (HMD800118) |
| 184.0 | 125.2 | 7 | Phosphorylcholine (HMD801565) |
| 184.0 | 166.1 | 5 | Phosphorylcholine (HMD801565) |
| 184.0 | 166.2 | 5 | Phosphorylcholine (HMD801565) |
| 185.0 | 166.8 | 5 | Vanylglycol (HMD801490) |
| 185.0 | 167.1 | 5 | Vanylglycol (HMD801490) |
| 188.0 | 171 | 10 | Acetylspermidine (HMD801276) |
| 192.5 | 176.5 | 8 | Isocitric acid (HMD800193) |
| 192.8 | 135 | 10 | 5-Hydroxyindoleacetic acid/5-Methoxytryptophol/Isocitric acid |
| 192.8 | 175.1 | 5 | 5-Hydroxyindoleacetic acid/5-Methoxytryptophol/Isocitric acid |
| 192.8 | 175 | 5 | 5-Hydroxyindoleacetic acid/5-Methoxytryptophol/Isocitric acid |
| 195.0 | 99.2 | 18 | Caffeine (HMD801847) |
| 195.0 | 158.9 | 7 | Not Assigned |
| 196.0 | 136.1 | 5 | Not Assigned |
| 196.0 | 159.8 | 5 | Not Assigned |
| 196.0 | 178.9 | 5 | Not Assigned |
| 196.9 | 81.1 | 6 | L-Dopa (HMD800181) |
| 197.0 | 179.1 | 5 | L-Dopa (HMD800181) |
| 198.0 | 180.3 | 7 | L-Dopa (HMD800181) |
| 199.0 | 81.2 | 10 | Erythrose-4-P (HMD801321) |
| 205.0 | 145.2 | 10 | L-Tryptophan (HMD800929) |
| 205.0 | 187.1 | 5 | L-Tryptophan (HMD800929) |
| 219.0 | 201 | 5 | Pantothenic acid/N-acetylserotonin (HMD801238) |
| 219.1 | 159.1 | 13 | Pantothenic acid/N-acetylserotonin (HMD801238) |
| 219.3 | 202.3 | 8 | Pantothenic acid/N-acetylserotonin (HMD801238) |
| 220.0 | 201.9 | 5 | Pantothenic acid (HMD800210) |
| 225.0 | 164.7 | 5 | Not Assigned |
| 225.0 | 105.1 | 11 | Not Assigned |
| 228.0 | 210.1 | 7 | Not Assigned |
| 285.0 | 105 | 20 | Not Assigned |
| 285.0 | 225 | 5 | Not Assigned |
| 289.0 | 271 | 8 | Not Assigned |
| 290.9 | 273 | 5 | Androsterone (HMD800031) |
| 328.9 | 246.8 | 5 | Not Assigned |
| 338.8 | 81.1 | 21 | Not Assigned |
| 338.8 | 256.8 | 10 | Not Assigned |
| 344.0 | 224.2 | 6 | Not Assigned |
| 344.0 | 283.5 | 5 | cGMP (HMD801314) |
| 346.0 | 285.6 | 7 | cGMP (HMD801314) |
| 386.0 | 303.9 | 8 | Not Assigned |
| 386.3 | 371.3 | 8 | Not Assigned |
| 386.7 | 244.7 | 10 | Not Assigned |
| 386.9 | 247 | 11 | Not Assigned |
| 386.9 | 326.5 | 7 | Not assigned |
| 387.0 | 245 | 12 | Not assigned |
| 387.2 | 371.2 | 8 | Not assigned |
| 403.8 | 288.2 | 17 | Not Assigned |
| 407.1 | 347 | 12 | Not assigned |
| 442.2 | 360.3 | 5 | Not assigned |
| 448.0 | 388.5 | 5 | Not assigned |
| 471.9 | 359 | 14 | Not assigned |
| 514.6 | 398.7 | 13 | Not assigned |
| 522.9 | 342.9 | 6 | Not assigned |
| 678.1 | 618.3 | 12 | Not assigned |

Notes:
*Most of the attributed compounds have been already reported in the CSF metabolome database (http://www.csfmetabolome.ca/).
Parent ions and fragments matched MS/MS mass spectra from the human metabolome database (http://www.hmdb.ca).

Each MRM was scanned for 0.10 sec using a 0.7 Da isolation window and optimized values for collision energy (CE) and tube lens (TL) voltages. Ten scans per MRM were summed to obtain the final intensity value of each MRM. A minimum of three replicates was recorded for each sample.

The final method was applied to the BioFIND samples. Details on the gender, age, years of diagnosis and staging of the patients for the BioFIND samples are shown in FIG. 5.

Example 2

Data Processing

Ion intensities of each MRM were normalized to the ion intensity of the MRM of endogenous arginine because this compound has been reported to present stable levels in human CSF even in the presence of neurodegenerative conditions. Experiments indicated that the use of endogenous arginine as a calibrator was appropriate since comparable discrimination and homogeneity was observed after multivariate analysis for three replicates performed on three different days. Also, arginine spiked into artificial CSF at different physiological concentration levels showed linearity in the concentration response (FIGS. 6A-C).

Most relevant MRMs indicated by principal component analysis (PCA) were manually combined into equations and ratios using the BioFIND testing set samples. The six ratios/equations presenting AUC>0.68 and the MRM 188->171 (parent->fragment) (Table 3) were used for the multivariate ROC. By the MRM profiling method, 67% (40 CSF out of 60 samples) of the BioFIND validation set (presented to the ROC curve as new samples) were correctly assigned.

TABLE 3

List of MRM, MRM ratios or MRM equations manually selected for the multivariate ROC curve, with correspondent AUC and fold change (HC/PD)

| MRM/MRM ratio/ MRM equation | AUC | fold change |
|---|---|---|
| (134.1 -> 72.4 + 177 -> 159.1 + 76.2 -> 59.4 + 184 -> 125.2)/ 188 -> 171 | 0.75 | 0.4 |
| 184 -> 125.2/188 -> 171 | 0.73 | 0.5 |
| (76.2 -> 59.4 + 134.1 -> 72.4 + 184 -> 125.2 + 386 -> 303.9)/ 188 -> 171 | 0.72 | 0.9 |
| (134.1 -> 72.4 + 177 -> 159.1)/ 188 -> 171 | 0.71 | 0.4 |
| 188 -> 171 | 0.7 | −0.4 |
| [(78.2 -> 61.5 + 79.2 -> 61.5 + 116.1 -> 88.2 + 188 -> 171) − (76.2 -> 59.4 + 134.1 -> 72.4 + 184 -> 125.2 + 386 -> 303.9)]/188 -> 171 | 0.69 | −6.4 |
| 134.1 -> 72.4/188 -> 171 | 0.68 | 2.1 |

What is claimed is:

1. A method for screening for Parkinson's disease, the method comprising:
   ionizing a human body fluid sample of cerebrospinal fluid;
   monitoring by mass spectrometry specific transitions connecting one or more ion pairs within the sample in order to generate a multidimensional chemical profile of the sample wherein the multidimensional chemical profile of the sample comprises a sum of an abundance of each of the ion pairs selected from the group consisting of: 134.1→72.4; 177→141.1; 76.2→59.4; and 184→125.2, divided by an abundance of the ion pair 188→171; and
   comparing the multidimensional chemical profile of the sample to a database of reference multidimensional chemical profiles, wherein each reference multidimensional chemical profile is produced from a training set of data, thereby screening for Parkinson's disease.

2. The method according to claim 1, wherein ionizing is by an ambient ionization technique.

3. The method according to claim 2, wherein the ambient ionization technique is paper spray ionization or electrosonic spray ionization.

4. The method according to claim 1, wherein the sample is a biological sample, and the training set of data is from a population of patients with a known disease status.

5. The method according to claim 1, wherein the multidimensional chemical profile of the sample comprises an abundance of the ion pair 188→171.

6. The method according to claim 5, wherein the ion pair 188→171 represents N8-or N1-acetylspermidine.

7. A method for screening for Parkinson's disease, the method comprising:
   receiving, to a computer, mass spectrometry data on a sample obtained by multiple reaction monitoring, wherein the mass spectrometry data comprises specific transitions connecting one or more ion pairs within the sample, and the sample is a human body fluid sample of cerebrospinal fluid;
   applying, via the computer, an unsupervised multivariate analysis to the mass spectrometry data in order to generate a multidimensional chemical profile of the sample wherein the multidimensional chemical profile of the sample comprises a sum of an abundance of each of the ion pairs selected from the group consisting of: 134.1→72.4, 177→141.1, 76.2→59.4, and 184→125.2, divided by an abundance of the ion pair 188→171; and
   comparing, via the computer, the multidimensional chemical profile of the sample to a database of reference multidimensional chemical profiles, wherein each reference multidimensional chemical profile is produced from a training set of data that comprises a population of patients with a known disease status, thereby screening for Parkinson's disease.

8. The method according to claim 7, wherein prior to the receiving step, the method further comprises:
   ionizing the sample to produce an ionized sample; and
   analyzing the ionized sample using multiple reaction monitoring mass spectrometry.

9. The method according to claim 8, wherein ionizing is by an ambient ionization technique.

10. The method according to claim 9, wherein the ambient ionization technique is paper spray ionization or electrosonic spray ionization.

11. The method according to claim 7, wherein the multidimensional chemical profile of the sample comprises an abundance of the ion pair 188→171.

12. The method according to claim 11, wherein the ion pair 188→171 represents N8-or N1-acetylspermidine.

* * * * *